United States Patent [19]

Kam et al.

[11] 4,252,783

[45] Feb. 24, 1981

[54] REDUCING FLUORESCENT BACKGROUND IN FLUORESCENT IMMUNOASSAYS

[75] Inventors: Jean Kam, Sunnyvale; Robert A. Yoshida, Mountain View, both of Calif.

[73] Assignee: Syva Company, Palo Alto, Calif.

[21] Appl. No.: 49,540

[22] Filed: Jun. 18, 1979

[51] Int. Cl.³ .................... G01N 33/52; G01N 1/00
[52] U.S. Cl. .................................... 424/8; 23/230 B; 250/302; 424/7; 424/11; 424/12; 424/13; 435/7
[58] Field of Search .................. 424/3, 7, 8, 11, 12, 424/13; 435/7; 23/230 B; 250/302

[56] References Cited

U.S. PATENT DOCUMENTS 3,689,633  9/1972  Sanae ............................... 424/12
4,121,975  10/1978  Ullman ........................... 424/12 X Primary Examiner—Anna P. Fagelson
Attorney, Agent, or Firm—Bertram I. Rowland

[57] ABSTRACT

Background fluorescence which interferes with the measurement of an analyte in fluorescent immunoassays in serum samples is substantially diminished by treating the serum sample with a sufficient amount of a peroxidic compound, either organic or inorganic, for a time sufficient to reduce the background fluorescence contributed by serum components. The peroxidic compound is readily quenched, without adversely affecting the assay composition.

9 Claims, No Drawings

REDUCING FLUORESCENT BACKGROUND IN FLUORESCENT IMMUNOASSAYS

BACKGROUND OF THE INVENTION

1. Field of the Invention

The use of fluorescent labels for the determination of analytes in immunoassays has shown substantial promise and numerous immunoassays have been developed which are dependent upon the accurate measurement of the fluorescence from an assay medium. One of the problems with fluorescence is the number of factors which contribute to background values. Included among these facts are light scatter, instrument variation, fluorescent reagent contamination, and endogeneous fluorescence in the sample.

The endogenous fluorescence can be a serious factor in diminishing the quantitative character of the assay. In many situations, the endogenous fluorescence will vary from sample to sample and will be different in the analyte samples from the standards or calibrators which are employed to provide for translating the observed fluorescent signal into the concentration of the analyte. In order to enhance the accuracy of the assay, it is desirable to diminish or completely remove the contribution of the endogenous fluorescent material to the observed signal during the immunoassay.

2. Description of the Prior Art

Illustrative immunoassays employing fluorescers as a label may be found in U.S. Pat. Nos. 3,998,943; 3,939,350; 3,996,345; and patents cited therein. Helman, et al., Clin. Chem. 20 1193, (1974) published the use of basic hydrogen peroxide for decolorizing hemolyzed and jaundiced serum samples. For background material see, Guilbault, "Practical Fluorescence," Marcel Dekker, New York (1973). An article on the fluorescence of bilirubin is Roth, M., Clin. Chim. ACTA, 17:48F (1967).

SUMMARY OF THE INVENTION

Endogenous fluorescence in serum samples which are assayed for an analyte by employing a fluorescent label is diminished by treating the serum sample with a sufficient amount of a peroxide compound for a time sufficient to substantially diminish the fluorescence capability of the serum sample. Particularly, peracetic acid and persulfate find use under mild conditions, followed by quenching of the peracid without adverse effects on the quantitative nature of the assay.

DESCRIPTION OF THE SPECIFIC EMBODIMENTS

A method is provided for diminishing endogenous fluorescence in serum samples for use in assays for the determination of analytes employing a fluorescent label. The reduction is greater than about 30%, more usually greater than about 50%, and preferably greater than about 70%, with excitation at about 490 to 500 nm and emission measured at about 510 to 530 nm. The method employs contacting at a pH greater than six a serum sample with a peracid, either organic or inorganic, in an aqueous medium. For the most part, the peracids are organic percarboxylic acids of from about one to seven carbon atoms, preferably of from one to three carbon atoms, or persulfate.

The amount of peracid employed per milliliter of serum may be varied widely, depending upon the peracid, the period of treatment, as well as the degree of reduction in endogenous fluorescence desired.

The amount of peracid employed will generally be from about 0.01 mmole to 10 mmole per ml of serum, more usually about 0.1 mmole to 5 mmole per ml of serum. For the organic peracids, the range will generally be from about 0.01 to 10 mmole per ml. For the inorganic acids, the range will generally be from about 0.05 to 10 mmole per ml, more usually from about 0.1 to 5 mmole per ml. The concentration of the peracid during the incubation with the serum will also vary widely, generally ranging from about 0.01 M to about 1.0 M, more usually from about 0.1 M to about 0.5 M. For the organic peracid, the range will generally be from about 0.05 M to 1.0 M, more usually from about 0.1 M to 0.5 M. For the inorganic acid, the concentration will generally be from about 5 mM to 0.2 M, more usually from about 10 mM to about 0.2 M.

The pH will normally be greater than six, usually greater than 6.5, generally from about 7 to 11, more usually from about 7 to 10. For the organic acid, the pH is preferably from about 7 to 8.5, while for the inorganic acid, the pH is preferably from about 8.5 to 10.5.

Various buffers may be employed, such as borate, phosphate, glycine, carbonate, tris, and the like. Preferred buffers are borate and carbonate.

When buffer is employed, the concentration of buffer may vary widely, but should be sufficient to provide the desired pH. Usually, buffer concentrations will generally be from about 0.1 to 1 M, more usually about 0.1 to 0.5 M. The concentration of buffer is not critical and in the case of the organic acid, need not be included during the incubation step.

The treatment method requires combining the serum sample, the peracid, conveniently as an aqueous solution, and, as desired, buffer. The serum may be subjected to prior treatment, such as filtration, centrifugation, or the like. The peracid will normally be added as its salt, rather than neutralizing upon combination with the serum.

The combined serum and peracid will then be incubated for at least about 1 min, usually not more than about 6 hrs, preferably from about 5 min to 1 hr, more usually from about 10 to 30 min. The particular incubation time, once past the minimum, is a matter of convenience, and will vary in relation to the amount of peracid used, the amount of endogenous fluorescence present and the rate at which the fluorescence is reduced by interaction with the peracid and the stability of the analyte.

After incubation, the peracid is quenched, conveniently by a reductant, such as sodium sulfite or dithionite. The sodium sulfite will be added as an aqueous solution, generally at a concentration of about 0.1 to 1 M, in an amount sufficient to destroy all of the residual peracid.

The various volumes employed will be determined by the permissible dilution of the serum for use in the assay sample. Therefore, the particular concentrations employed, the ratios of volumes of serum, peracid, buffer, and quenching agent, will all be related to the final volume of the assay sample and the desired concentration of the serum in the sample.

Optionally, after treatment with the peracid, the assay sample may be further treated by employing a combination of oleate, α-cyclodextrin and glycerol. The concentration of oleate in the assay medium will generally vary from about 0.05 to 5, more usually from about 0.1 to 1 mM. The amount of α-cyclodextrin in the assay medium will generally be from about 0.1 to 1 weight percent, more usually from about 0.1 to 0.5 weight percent. The amount of glycerol in the assay medium will normally be from about 0.1 to 20 weight percent, more usually from about 0.5 to 15 weight percent and preferably about 10 weight percent. The pH during the treatment with these reagents will generally be from about 8 to 10.5, more usually from about 8.5 to 10. The combination will usually be incubated generally for at least about 5 min and usually not more than about 3 hrs, preferably from about 10 min to 1 hr, and more preferably about 30 min.

The materials are combined and agitated in order to insure substantially uniform dispersion, and the mixture incubated at ambient temperatures for the indicated period of time. After the treatment, the assay may then be made directly on the sample by adding whatever appropriate reagents are required for the assay determination.

Illustrative organic peracids include peracetic acid, percarbonic acid ethyl ester, performic acid, and perpropionic acid. For the inorganic acid, potassium persulfate may be employed, although any convenient counterion may be employed, particularly any alkali metal cation.

EXPERIMENTAL

The following examples are offered by way of illustration and not by way of limitation.

The following protocol was employed for an assay. A mixture was prepared containing 10 μl of serum or 10 μl of PBS, 10 μl of PBS, 0.40 ml of 0.25 M carbonate, pH 9.5, and 50 μl of 0.5 M KHSO$_5$, pH 4. The mixture was incubated for 5 min at room temperature, followed by the addition of 50 μl of 0.5 M, sodium sulfite. After agitating the mixture, 10 μl of PBS was added plus 0.5 ml of 1.0 mM oleate, 0.5% α-cyclodextrin and 20% glycerol in 0.10 M glycine-NaOH containing 0.01% sodium azide, pH 9.4. The mixture was incubated for 30 min. at room temperature, vortexed, and the fluorescence determined on a PE Model 1000 Fluorimeter $\lambda_{ex}=491$ nm and $\lambda_{em}=519$ nm, with Baird-Atomic bandpass filters, sensitivity ×300, slit-open, at ambient temperatures. Of the 29 samples, the average background fluorescence after substracting for the blank was 30.3±14.9.

In a second series, varying concentrations of persulfate were employed. The protocol employed was to combine 10 μl of the serum sample or 10 μl of PBS, 10 μl of deionized water or the appropriate amount of 0.50 M potassium persulfate, 0.60 ml of 0.1 M carbonate containing 0.01% sodium azide, pH 9.5, agitating the mixture and incubating for 15 min at room temperature. At the end of this time, 10 μl of 1.5 M sodium sulfite plus 0.3 ml of 0.1 M carbonate containing 0.01% sodium azide, pH 9.5 was added, the mixture agitated, and the fluorescence determined as described above. The following table indicates the results.

TABLE I

| % Serum assay | KHSO$_5$ mM | <F>* | <F>- Blank** | % Reduction in $F^{519nm}$ |
|---|---|---|---|---|
| 1.1 | 0 | 8517 | 8464 | 0 |
| 0 | 0 | 53 | 0 | |
| 1.1 | 5.4 | 93 | 49 | 99.4 |
| 0 | 5.4 | 44 | 0 | |
| 1.1 | 11 | 76 | 33 | 99.6 |
| 0 | 11 | 43 | 0 | |

TABLE I-continued

| % Serum assay | KHSO$_5$ mM | <F>* | <F>- Blank** | % Reduction in $F^{519nm}$ |
|---|---|---|---|---|
| 1.1 | 32 | 73 | 29 | 99.7 |
| 0 | 32 | 45 | 0 | |

*average of 2-3 readings
**volume corrected

It is evident from the above results, that the persulfate treatment substantially diminishes the background fluorescence resulting from serum.

In the next study, sodium peracetate was employed. The protocol was as follows. All serum samples were centifuged at 10 K rpm for 15 min and precipitates were discarded. The serum supernatants were Millipore filtered twice (0.22 micron cellulose mixed ester filters) and 0.05% sodium azide and 0.01% thimerosal were added as preservatives.

To 15 μl of 40% peracetic acid in a 3 ml glass vial was added with vigorous stirring 76 μl of 2.5 M sodium hydroxide. To the mixture was then added slowly 500 μl of the filtered serum, the pH between between 7-8. After incubating for 15 min at room temperature with continuous stirring, 150 μl of 0.526 M sodium sulfite was added followed by the addition of 260 μl of 0.25 M pH 9.5 borate buffer to provide a 50% serum solution.

All fluorescence measurements were made on a Perkin-Elmer MPF-2A Fluorescence Spectrophotometer, fitted with Baird-Atomic filters, with the $\lambda_{ex}$ at 482 nm and the $\lambda_{em}$ at 490-530 nm. The emission and excitation slits were adjusted to keep the highest peak on scale. The sensitivity setting was at position six. A 0.5 ml sample cuvette with a 0.5 cm light path was used for all measurements.

In a first study, a humanIgG conjugate with fluorescein was employed, having a dye/protein ratio of about 5.5. Each measured mixture contained 0.28% BSA in 0.25 M borate, pH 9.5. The fluorescence intensity of the conjugate was determined in the presence of 5% treated Monitrol IX sera and sheep serum, either treated or untreated at a concentration of 5% of the assay medium. It was found that when the conjugate is combined with the untreated sera, the readings which result are somewhat less than the sum of the serum itself and the conjugate by itself in borate buffer.

The following table reports the results.

TABLE II

| FHIgG[1] conc. protein M × 10$^{-9}$ | Serum sample No. | % Sera | Normalized Fluorescence Reading | | |
|---|---|---|---|---|---|
| | | | 0 | 5 untreated | treated |
| 5 | — | | 100 | | |
| 0 | 1 | | | 13.6 | 2.4 |
| 5 | 1 | | | 110 | 105 |
| 0 | 2 | | | 20.7 | 4.8 |
| 5 | 2 | | | 116 | 105 |
| 0 | 3 | | | 21.3 | 3.6 |
| 5 | 3 | | | 117 | 105 |
| 0 | 4 | | | 31.4 | 4.7 |
| 5 | 4 | | | 128 | 106 |
| 5 | — | | 100 | — | — |
| 0 | Monitrol IX | | | 45.6 | 8.2 |
| 5 | Monitrol IX | | | 144.5 | 107.5 |

[1]FHIgG-fluorescein-human immunogammaglobulin 5.5 fluoresceins/protein molecule It is evident from the above results, that treatment of the serum with a peracid, greatly enhances the reproducibility of the fluorescence measurement, while substantially reducing the background, when a fluorescent reagent is present in the assay sample with the serum.

Using the fluorescein conjugate described above and rabbit antibody to HIgG to which rhodamine had been conjugated, an assay was performed, employing $5 \times 10^{-9}$ M of the fluorescein conjugate and $2 \times 10^{-8}$ M of the rhodamine conjugate in conjunction with 5% treated sheep serum plus 0.28% BSA in 0.25 M borate buffer, pH 9.5, with a final volume of 0.5 ml. The free HIgG concentration was varied between 5 and $15 \times 10^{-9}$ M. (It should be noted that the reagents employed had been stored for a considerable length of time, and therefore did not provide optimum sensitivity.) The following table indicates the results.

TABLE III

| FHIgG[1] conc. $M \times 10^9$ | RAb[2] conc. $M \times 10^8$ | HIgG conc. $M \times 10^9$ | Normalized Chart Unit | |
|---|---|---|---|---|
| | | | no serum | 5% treated serum |
| — | — | — | 0 | 7.5 |
| 5 | — | — | 100 | 110 |
| " | 2 | — | 73 | 82.5 |
| " | " | 5 | 86 | 99.5 |
| " | " | 10 | 91 | 102 |
| " | " | 15 | 96.5 | 105 |

[1] FHIgG-fluorescein conjugate to human immunogammaglobulin with a dye/protein ratio of 5.5.
[2] RAb-rhodamine conjugate to rabbit antibody to HIgG.

It is evident from the above results, that an assay can be carried out for human immunogammaglobulin whereby a sufficient spread can be obtained over a three-fold concentration variation at extremely low concentrations of the analyte. By treating the serum, one can reduce the background, as well as inhibit variations between calibrators and samples.

In accordance with the subject invention, a method is provided for reducing endogenous fluorescence resulting from serum in immunoassays involving a fluorescent label. The method of treatment of the serum does not adversely affect the assay, so that the necessary fluorescent reagents can be added without their degradation or adverse nonspecific interactions. The method is simple, rapid, and can be used with a wide variety of analytes, which are not sensitive to the peroxide treatment under the mild conditions employed.

Although the foregoing invention has been described in some detail by way of illustration and example for purposes of clarity of understanding, it will be obvious that certain changes and modifications may be practiced within the scope of the appended claims.

What is claimed is:

1. In a method for determining the presence of an analyte in a serum sample, wherein the amount of analyte is related to the amount of fluorescence from said sample medium, the improvement which comprises:
   contacting said analyte containing serum sample in a medium at a pH of at least about 6.5 with a peracid in an amount sufficient to substantially reduce the endogenous fluorescence of said serum sample.

2. A method according to claim 1, wherein said peracid is organic.

3. A method according to claim 1, wherein said peracid is inorganic.

4. In an immunoassay method for determining the presence of an analyte in a serum sample, where a fluorescent label is employed bound to either a ligand or receptor and the amount of fluorescence is related to the amount of the sample, the improvement which comprises:
   contacting said serum sample with from about 0.01 mmole to 10 mmole of peracid per ml of serum at a pH of at least about 6.5 for a time sufficient to substantially reduce fluorescence endogenous to said serum; and destroying excess peracid with a chemical reductant,
   to provide a sample for analysis having substantially reduced endogenous fluorescence.

5. A method according to claim 4, wherein said peracid is a percarboxylic acid, the pH is in the range of about 7 to 8.5, and the amount of peracid is from about 0.01 to 1 mmole per ml.

6. A method according to claim 5, wherein said peracid is peracetate.

7. A method according to claim 4, wherein said peracid is an inorganic acid, the pH is in the range of about 8.5 to 10.5, and the peracid is present in from about 0.05 to 10 mmole per ml.

8. A method according to claim 7, wherein said inorganic acid is persulfate.

9. A method according to any of claims 4 to 8, wherein said sample having substantially reduced endogenous fluorescence is treated with α-cyclodextrin prior to measurement of said analyte.

* * * * *